(12) United States Patent
Fieselmann et al.

(10) Patent No.: US 10,660,581 B2
(45) Date of Patent: May 26, 2020

(54) METHOD FOR OPERATING AN X-RAY DEVICE, X-RAY DEVICE, COMPUTER PROGRAM AND ELECTRONICALLY READABLE STORAGE MEDIUM

(71) Applicant: Siemens Healthcare GmbH, Erlangen (DE)

(72) Inventors: Andreas Fieselmann, Erlangen (DE); Ludwig Ritschl, Erlangen (DE); Julia Wicklein, Neunkirchen a. Br. (DE); Magdalena Herbst, Pinzberg (DE); Christoph Luckner, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/519,129

(22) Filed: Jul. 23, 2019

(65) Prior Publication Data

US 2020/0029916 A1 Jan. 30, 2020

(51) Int. Cl.
*A61B 6/00* (2006.01)
*A61B 6/02* (2006.01)

(52) U.S. Cl.
CPC .............. *A61B 6/025* (2013.01); *A61B 6/405* (2013.01); *A61B 6/466* (2013.01); *A61B 6/542* (2013.01)

(58) Field of Classification Search
CPC .............................. A61B 6/5241; A61B 6/469
See application file for complete search history.

(56) References Cited

U.S. PATENT DOCUMENTS

| 5,123,056 A * | 6/1992 | Wilson ................. A61B 6/4476 348/E5.089 |
| 8,693,622 B2 | 4/2014 | Graumann et al. |
| 2008/0152088 A1* | 6/2008 | Wang ....................... A61B 6/02 378/98.12 |
| 2012/0051498 A1 | 3/2012 | Koishi |

(Continued)

FOREIGN PATENT DOCUMENTS

| DE | 4102729 A1 | 8/1991 |
| DE | 102016205176 A1 | 10/2017 |

OTHER PUBLICATIONS

German Office Action dated Apr. 15, 2019 for German Application No. 102018212389.6 and English Translation thereof.
(Continued)

*Primary Examiner* — Dani Fox
(74) *Attorney, Agent, or Firm* — Harness, Dickey & Pierce, P.L.C.

(57) ABSTRACT

A method is for operating an X-ray device. In an embodiment, the method includes acquiring a sequence of images of a patient; moving an acquisition arrangement including at least one X-ray tube assembly, during the acquiring of the sequence of images, along the patient in a scanning direction; evaluating at least two different images, showing at least one common feature of the patient, to determine depth information for the at least one common feature; and actuating a collimator aperture of a collimator of the X-ray tube assembly, as a function of position information describing a position of the acquisition arrangement in the scanning direction, to change an aperture angle of a radiation field generated by the X-ray tube assembly in the scanning direction.

21 Claims, 4 Drawing Sheets

(56) References Cited

U.S. PATENT DOCUMENTS

2017/0281109 A1    10/2017   Ecabert et al.

OTHER PUBLICATIONS

German Decision to Grant dated Sep. 23, 2019 for German Application No. 102018212389.6 and English Translation thereof.
Shibata, Koichi et al.: "Parallel-scanning tomosynthesis using a slot scanning technique: Fixed-focus reconstruction and the resulting image quality"; in: Medical Physics; vol. 41; No. 11; 2014; DOI: https://doi.org/10.1118/1.4896102.
"Slot Radiography"; in: www.shimadzu.com; May 22, 2018: https://www.shimadzu.com/med/products/app/od0gjn0000004agj.html.
German Office Action dated Apr. 15, 2019 for German Application No. 102018212389.6.

\* cited by examiner

METHOD FOR OPERATING AN X-RAY DEVICE, X-RAY DEVICE, COMPUTER PROGRAM AND ELECTRONICALLY READABLE STORAGE MEDIUM

PRIORITY STATEMENT

The present application hereby claims priority under 35 U.S.C. § 119 to German patent application number DE 102018212389.6 filed Jul. 25, 2018, the entire contents of which are hereby incorporated herein by reference.

FIELD

Embodiments of the invention generally relate to a method for operating an X-ray device, wherein a sequence of images of a patient is acquired and during the acquisition of the sequence of images an acquisition arrangement comprising at least one X-ray tube assembly moves along the patient in a scanning direction, wherein at least two different images showing the same feature of the patient are evaluated in order to determine depth information for at least one of the features; and to an X-ray device, a computer program and an electronically readable storage medium.

BACKGROUND

In order to investigate and diagnose orthopedic issues, X-ray images of a patient are often acquired which show a relatively long section of the patient's body, for example the vertebral column or a leg from the hip to the foot. Slot-scan radiography (SSR), for example, can be used for acquiring images of the type. In SSR, X-ray tube and X-ray detector are moved simultaneously along an axis of the patient while the X-ray beam is highly collimated into a slit. Owing to the strong collimation, i.e. because of the small aperture angle of the radiation field generated by the X-ray tube, the scattered radiation produced during the image acquisition is reduced, with the result that the patient is exposed to a smaller radiation dose compared to one or more composite standard radiographic images, while image quality is comparable.

A further scanning technique for acquisition of images of longer sections of the body is provided by parallel-scan tomosynthesis (PST). Compared with SSR, PST offers the advantage that a 3D tomosynthesis dataset can be generated by reconstruction, thereby enabling the overlapping of anatomical structures to be at least partially reduced. To that end, the collimator of an X-ray source is adjusted in such a way that a comparatively large aperture angle of the generated radiation field is produced. The image acquisition is then performed in such a way that as large an area of overlap as possible of the radiation field is obtained between the individual scans during an acquisition of a sequence of images. This enables 3D information to be generated during the scanning of anatomical features of the patient from different viewing directions. A method of such a type is described in U.S. Pat. No. 8,693,622 B2, for example.

SUMMARY

However, the inventors have discovered that compared with SSR, PST has a disadvantage that the patient is exposed to a higher radiation dose during the image acquisition due to the overlapping radiation fields.

At least one embodiment of the invention is therefore directed to an improved method for operating an X-ray device which enables images to be acquired with associated depth information while minimizing radiation exposure for the patient.

At least one embodiment of the invention is therefore directed to a method for operating an X-ray device, the method comprising:
acquiring a sequence of images of a patient;
moving an acquisition arrangement including at least one X-ray tube assembly, during the acquiring of the sequence of images, along the patient in a scanning direction;
evaluating at least two different images, showing at least one common feature of the patient, to determine depth information for the at least one common feature; and
actuating a collimator aperture of a collimator of the X-ray tube assembly, as a function of position information describing a position of the acquisition arrangement in the scanning direction, to change an aperture angle of a radiation field generated by the X-ray tube assembly in the scanning direction.

According to at least one embodiment of the invention, a collimator aperture of a collimator of the X-ray tube assembly is actuated in the scanning direction as a function of position information describing the position of the acquisition arrangement in order to change an aperture angle of a radiation field generated by the X-ray tube assembly in the scanning direction.

For an X-ray device according to at least one embodiment of the invention, it is provided that the device comprises a computing device and an acquisition arrangement, the acquisition arrangement comprising at least one X-ray tube assembly having a collimator and the computing device being configured for carrying out a method according to at least one embodiment of the invention.

For an X-ray device according to at least one embodiment of the invention, it is provided that the device comprises
an acquisition arrangement, including at least one X-ray tube assembly having a collimator; and
a computing device, configured to
acquire a sequence of images of a patient;
move an acquisition arrangement including at least one X-ray tube assembly, during the acquiring of the sequence of images, along the patient in a scanning direction;
evaluate at least two different images, showing at least one common feature of the patient, to determine depth information for the at least one common feature; and
actuate a collimator aperture of a collimator of the X-ray tube assembly, as a function of position information describing a position of the acquisition arrangement in the scanning direction, to change an aperture angle of a radiation field generated by the X-ray tube assembly in the scanning direction.

For a computer program according to at least one embodiment of the invention, it is provided that the program comprises instructions which, when executed by a computing device of an X-ray device, cause the computing device to carry out a method according to at least one embodiment of the invention.

For an electronically readable storage medium, it is provided according to at least one embodiment of the invention that a computer program according to at least one embodiment of the invention is stored thereon.

BRIEF DESCRIPTION OF THE DRAWINGS

Further advantages and details of the invention will become apparent from the example embodiments described in the following, as well as with reference to the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention, a collimator aperture of a collimator of the X-ray tube assembly is actuated in the scanning direction as a function of position information describing the position of the acquisition arrangement in order to change an aperture angle of a radiation field generated by the X-ray tube assembly in the scanning direction.

A solution according to at least one embodiment of the invention offers an advantage that different anatomical structures and/or features of the patient can be imaged along the scanning direction using radiation fields expanded to different widths such that depth information relating to a feature shown in at least two images taken from different viewing angles can be obtained from the resulting images. At the same time, however, images can be acquired during the image acquisition in regions of the patient in which depth information is not necessary owing to the examination objective or the anatomical makeup of the region using a reduced collimator aperture and consequently a smaller aperture angle of the radiation field. This advantageously enables the radiation dose to which the patient is exposed to be reduced during the image acquisition in the regions, as well as, considered as a whole, for the entire acquisition of the sequence of images.

The method according to at least one embodiment of the invention therefore enables images to be acquired during an acquisition of a sequence of images of a patient along a scanning direction as a function of the position of the acquisition arrangement either using a radiation field with a wider aperture angle in order to obtain depth information or using a narrower radiation field in order to reduce the radiation dose. This advantageously enables images to be acquired using a radiation field with a wider aperture angle only in the regions in which depth information is also required subsequently, and to reduce the radiation exposure for the patient in regions in which depth information is not required.

The X-ray tube assembly of the X-ray device generates in particular a fan beam or a cone beam, wherein the aperture angle can be changed in the scanning direction, i.e. in the direction along which the acquisition arrangement moves during the acquisition of the sequence of images, by actuating the collimator of the radiation source.

In the process, the individual images of the sequence of images are generated in each case at different positions of the acquisition arrangement such that the images in each case visualize a different part or a different section of the patient. The degree of overlap between the individual sequentially acquired images is dependent here not only on the distance between the positions of the acquisition arrangement but also on the aperture angle, such that a large overlap between the scanned areas of individual sequentially acquired images can be used in regions in which depth information is to be generated, and the area of overlap can be reduced as far as possible in regions in which no depth information is required. A small area of overlap between individual sequentially acquired images can of course also remain in the regions in which no depth information is to be generated so that the images can subsequently be assembled into a composite image, for example by image stitching.

The relative positioning between the acquisition arrangement and the patient changes during the acquisition of the sequence of images. It is possible in this case that the acquisition arrangement moves along a stationary patient or that the acquisition arrangement is stationary and the patient is moved relative to the acquisition arrangement. A movement of patient and acquisition arrangement in such a way that the acquisition arrangement moves relative to the patient is also conceivable. The patient can be positioned in the X-ray device either upright or lying supine on a corresponding patient support and positioning device.

It can be provided according to at least one embodiment of the invention that the position information describes an anatomical position describing a current positioning of the acquisition arrangement in relation to the patient. The relationship between the spatial position of the acquisition arrangement, i.e. its position along an axis running in the scanning direction, and the anatomical position, i.e. the positioning of the acquisition arrangement in relation to the patient, can depend for example on the size of the patient and how the patient is positioned in the X-ray device. The position information can therefore advantageously describe the anatomical position of the patient such that the collimator aperture can be adjusted according to the region of the patient that is currently to be scanned. The possibility to set the collimator aperture of the collimator of the X-ray tube assembly as a function of the anatomical position in relation to the patient enables individual anatomical regions to be scanned in a targeted manner using a comparatively wider aperture angle in order to generate depth information, and other anatomical regions for which no depth information is desired or necessary to be scanned using a lower aperture angle in order to reduce the radiation dose.

During the scan of a leg of the patient from the hip to the foot, for example, the collimator can be adjusted in such a way that depth information is generated for at least one anatomical feature of the patient only in the region of a hip joint, a knee joint and an ankle joint, i.e. images are acquired in these regions using a greater aperture angle of the radiation field. In the other regions, in particular in regions having a less complex anatomical structure, images can be acquired with a smaller aperture angle in order to reduce the radiation dose.

Thus, in the example of the scan of the leg in the region of the thigh and the lower leg of the patient, a smaller aperture angle can be used since only single, non-overlapping bones are present there over a comparatively great length. Selecting for which anatomical features depth information is generated and for which such information is not, in other words how the collimator is actuated as a function of the anatomical position, can be decided individually for each acquisition of a sequence of images and according to the purpose of the examination.

In order to determine the anatomical position of the patient, it can be provided according to at least one embodiment of the invention that the anatomical position is determined from image data acquired via an optical camera of the X-ray device and/or that the anatomical position is determined from at least one already acquired image of the sequence of images. In this case the optical camera can be mounted for example on the acquisition arrangement and thus be movable with the acquisition arrangement or it can be arranged as stationary on the X-ray device.

The image data generated by the camera shows the patient or a part of the patient. The image data can in this case also indicate the position of the acquisition arrangement and in particular be realtime image data. It is also possible for the image data to be generated from the current position of the acquisition arrangement as viewing angle, in particular in the case of an optical camera mounted on the acquisition arrangement. The current anatomical position of the acquisition arrangement can subsequently be determined from the image data generated by the optical camera. A 3D camera, for example, can be used in this case as the optical camera.

It is equally possible for the current anatomical position of the acquisition arrangement to be determined from at least one already acquired image of the sequence of images. For this purpose, the anatomical structures to be identified on the image can for example be assigned to an anatomical position of the patient.

The anatomical position can be determined for example by way of software and/or by way of a computing device of the X-ray device. In this case the anatomical region of the image acquired with the following X-ray scan can be predicted for example by way of a realtime analysis of the most recently acquired X-ray images. This can happen e.g. taking into account an anatomical atlas and the known physical proportions of the patient and/or taking into account already existing X-ray images. It is of course also possible for the anatomical position to be determined based on a combination of an evaluation of the image data obtained with an optical camera and an evaluation of most recently acquired X-ray images.

In addition or alternatively thereto, it is possible for the anatomical position to be determined from a spatial position describing a current distance of the acquisition arrangement from a start point or an end point of its movement. For this purpose, it can be provided that an assignment of anatomical positions to the spatial positions in the scanning direction is performed for example as a function of patient size and/or the positioning of the patient in the X-ray device. If, for example, the size of the patient is known and the patient is supported in a defined position, then the anatomical position of the patient corresponding to the current spatial position can be inferred as a function of the current distance of the acquisition arrangement from a start point or an end point of its movement in the scanning direction.

It can be provided according to at least one embodiment of the invention that different anatomical positions are assigned to different spatial positions via a user input into a computing device of the X-ray device and/or via a manual moving of the acquisition arrangement into a spatial position corresponding to an anatomical position. The user input can be entered for example by an operator of the X-ray device. The association between the anatomical position of the patient and the spatial position can be established for example via a measurement of the patient and a subsequent input of the measured values obtained by the measurement. In addition or alternatively thereto, it is possible for the acquisition arrangement to be moved manually into a spatial position, the spatial position thus set then being assigned to a specific anatomical position of the patient by way of a user input into the computing device, such that the corresponding anatomical positions for one or more spatial positions are known for a subsequent measurement.

It should be noted that in addition to the variants described here it is also possible generally to use an existing registration of the patient or a registration that is to be performed with the X-ray device, in particular if suchlike is provided in any case. In this instance, for example, a model of the patient can be positioned in the coordinate system of the X-ray device in which the current spatial position of the acquisition arrangement or of the patient couch is also present. Beneficially, a registration will be correctively aligned in the event of movements of the patient.

According to at least one embodiment of the invention, it can be provided that an anatomical landmark is determined from at least one image of the sequence of images, at least one item of depth information being determined for the anatomical landmark. The at least one item of depth information can be determined from at least two images showing the anatomical landmark. It can also be provided that multiple items of depth information are determined for an anatomical landmark, for example in order to mark the course of an extended landmark, or that multiple landmarks are determined from the images of the sequence, for which depth information is determined. In particular it can be provided that the anatomical landmarks are determined from the obtained images automatically by a computing device of the X-ray device, in particular also taking into account an image analysis of acquired images of the sequence. It is of course also possible to determine an anatomical landmark from at least one image of the sequence of images without taking into account or determining depth information associated with the landmark, for example when the landmark is used for a subsequent 2D measurement.

In a preferred embodiment of the invention, it can be provided that the collimator aperture is assigned to an anatomical position as a function of assignment information stored in particular in a computing device of the X-ray device. Thus, information can be stored in the X-ray device to indicate with which collimator aperture for an anatomical position in the case of a majority of patients of a representative patient group good results are possible in terms of the generation of depth information and/or the determining of an anatomical landmark are possible with a satisfactory degree of precision.

According to at least one embodiment of the invention, it can be provided that the collimator aperture of the collimator of the X-ray tube assembly is actuated orthogonally to the scanning direction as a function of the position information in order to change an aperture angle of the radiation field generated by the X-ray tube assembly. By varying the angle of the radiation field orthogonally to the scanning direction, it is possible to align the image acquisition to a relevant width of the region that is to be scanned. In this way the radiation exposure of the patient can be reduced further. The lateral collimation, i.e. the variation of the aperture angle orthogonally to the scanning direction, can be performed in particular according to the angle parallel to the scanning direction as a function of the anatomical position. In a scan of the vertebral column of the patient, for example, the collimator aperture can be adjusted in such a way that the ribs of the patient adjoining the vertebral column at the sides are not encompassed in the scan.

According to at least one embodiment of the invention, it can be provided that at least one further acquisition parameter of the X-ray device is varied in addition to the collimator aperture of the collimator of the X-ray tube assembly, in particular a scanning speed of the acquisition arrangement and/or an X-ray focus-patient distance and/or an electrical voltage of the X-ray tube assembly and/or the tube current-time product of the X-ray tube assembly being used as acquisition parameters. An assignment of a value of the acquisition parameter to a specific anatomical position can also be stored in the X-ray device in respect of the at least one further acquisition parameter. This advantageously makes it possible for the individual images of the sequence of images to be acquired according to the current anatomical position of the acquisition arrangement. In this way, the best possible image quality can be achieved for each individual image of the sequence of images and/or the radiation exposure can be reduced to a minimum for the patient.

It can be provided according to at least one embodiment of the invention that an acquisition arrangement is used comprising at least one X-ray detector disposed opposite the at least one X-ray tube assembly, an acquisition parameter of the at least one X-ray detector being set as a function of the position information. This enables not only the X-ray tube assembly but also the X-ray detector to be adjusted as a function of a current anatomical position of the patient, as a result of which the image quality of an image showing the anatomical structure present in the current anatomical position can be further increased.

It can furthermore be provided according to at least one embodiment of the invention that a collimator aperture of a collimator of the X-ray detector and/or a detector entrance dose and/or an X-ray focus-detector distance and/or an angle formed by a central ray of the radiation field and a detector normal of the X-ray detector are/is varied as acquisition parameter(s) of the X-ray detector. By varying the collimator aperture of the collimator of the X-ray detector it is possible for example to exert an influence on a shielding of scattered radiation, as a result of which an improvement in image quality can be achieved. Also changing the detector entrance dose and/or the X-ray focus-detector distance can not only improve the image quality of one or more acquired images but also contribute to a further reduction of the radiation exposure of the patient that is to be examined. The angle between the central ray of the radiation field and the detector normal of the X-ray detector can be changed by tilting the X-ray tube assembly and/or by tilting the X-ray detector. Also in relation to the collimator aperture of the collimator of the X-ray detector as well as to the detector entrance dose, the X-ray focus-detector distance and the angle between central ray and the detector normal, it can be provided that a respective assignment of corresponding values as a function of the anatomical position is stored in the X-ray device.

According to at least one embodiment of the invention, it can be provided that a synthetic radiographic image which is supplemented with at least one item of depth information of a relevant anatomical region as additional information is generated from the sequence of images and/or that a 3D tomosynthesis dataset is generated from the sequence of images. The sequence of images can be presented to a physician for example in a clear and time-saving manner in the form of a synthetic radiographic image. A 3D tomosynthesis dataset produced from the sequence of images can be used for example to perform a forward projection at points for which depth information is available for a different viewing angle from the viewing angle of the acquisition of the sequence of images. Structures overlapping one another in the acquired images or in the two-dimensional synthetic radiographic image generated from the images can thus be visualized in a differentiated manner in accordance with the depth information. The viewing angle for the forward projection can in this case be chosen as a function of the depth information, so that for example a spatial separation of the anatomical structures can be represented in an optimal manner. It is of course also possible to perform a forward projection at points for which no depth information is available on the basis of the 3D tomosynthesis dataset generated from the sequence of image data.

In addition or alternatively thereto, a synthetic radiographic image can be produced from the 3D tomosynthesis dataset by not including certain anatomical regions in the forward projection. To that end, the anatomical structures are first segmented in the 3D tomosynthesis dataset and the structures that are not relevant can be masked out. In this way, the overlaying of anatomical structures can be reduced in the synthetic radiographic image. In a scan of the vertebral column of the patient, for example, the ribs of the patient can be segmented and masked out.

It is also possible for the depth information to be represented for example by color coding of one or more anatomical features in the radiographic image. In addition or alternatively thereto, a 3D tomosynthesis dataset that contains, at least for a part of the scanned region, a three-dimensional representation of the anatomical structures of the patient located there can also be generated from the sequence of images. Various generally known reconstruction methods that make use of scans having different viewing angles can be used for this purpose.

For an X-ray device according to at least one embodiment of the invention, it is provided that the device comprises a computing device and an acquisition arrangement, the acquisition arrangement comprising at least one X-ray tube assembly having a collimator and the computing device being configured for carrying out a method according to at least one embodiment of the invention.

For a computer program according to at least one embodiment of the invention, it is provided that the program comprises instructions which, when executed by a computing device of an X-ray device, cause the computing device to carry out a method according to at least one embodiment of the invention.

For an electronically readable storage medium, it is provided according to at least one embodiment of the invention that a computer program according to at least one embodiment of the invention is stored thereon.

All of the advantages and embodiments explained in relation to the method according to embodiments of the invention are also applicable analogously to the X-ray device according to embodiments of the invention, the computer program according to embodiments of the invention, and the electronically readable storage medium according to embodiments of the invention.

Figure 1:
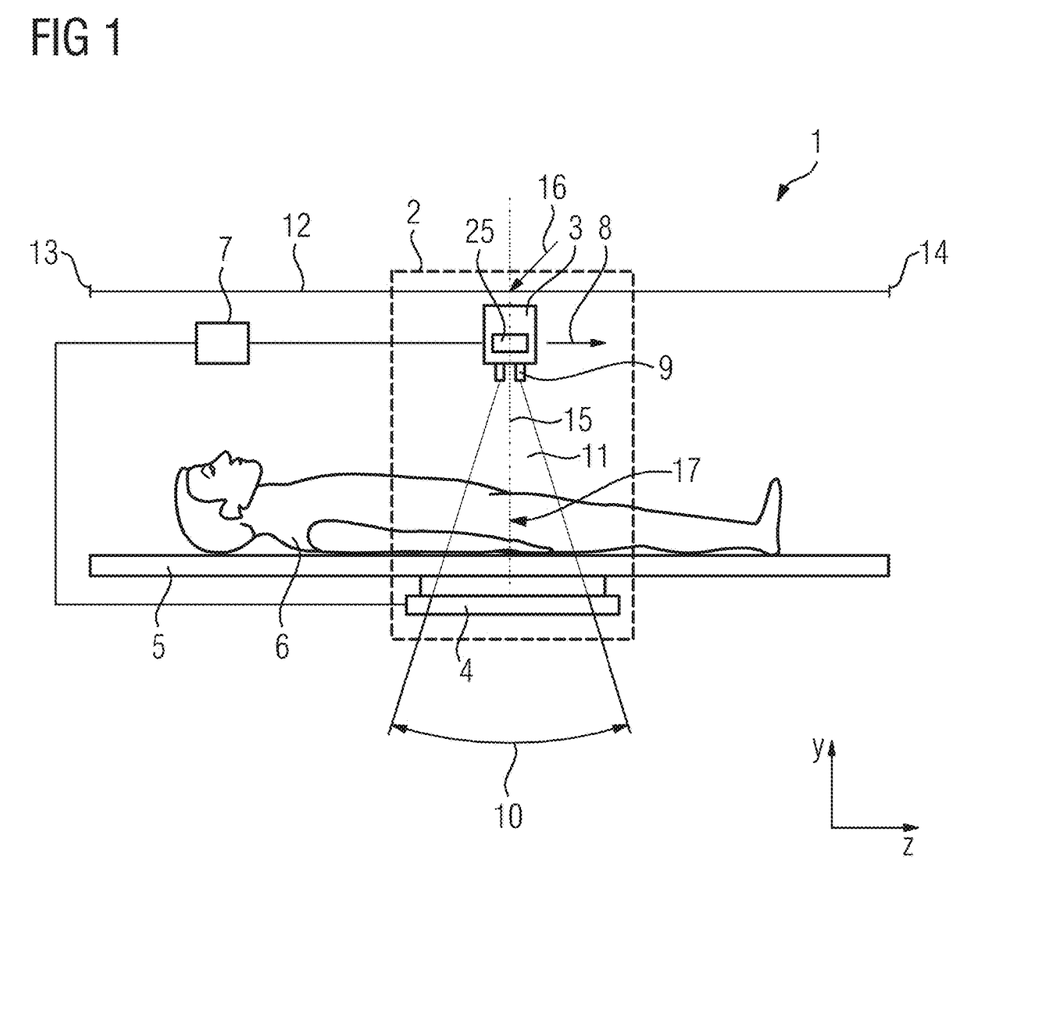
FIG. 1 shows a schematic representation of an X-ray device according to an embodiment of the invention.

FIG. 1 shows a schematic representation of an X-ray device 1 according to an embodiment of the invention. The X-ray device 1 comprises an acquisition arrangement 2, which in turn comprises an X-ray tube assembly 3 as well as an X-ray detector 4 arranged opposite the X-ray tube assembly 3. The X-ray device 1 further comprises a patient support and positioning device 5, which in this example embodiment is embodied as a patient couch and on which a patient 6 is positioned. The X-ray device 1 also comprises a computing device 7, which is connected to the X-ray tube assembly 3 and the detector 4. The acquisition arrangement 2 is movable along a scanning direction, which is symbolized by the arrow 8 and corresponds to the z-axis of the coordinate system shown in FIG. 1.

The X-ray tube assembly 3 can be embodied for example as an X-ray tube and comprises a collimator 9, which is implemented as adjustable. By adjusting the setting of the collimator 9 it is possible to vary the aperture angle 10 of a radiation field 11 generated by the X-ray tube assembly 3. The aperture angle 10 in this case denotes the aperture angle of the radiation field 11 embodied as a cone beam field or fan beam field in the scanning direction, in other words, in the example shown, it determines the expansion of the radiation field 11 in the z-direction.

The acquisition arrangement 2 can be moved in the scanning direction along an axis 12 which runs from a start point 13 to an end point 14. In this example embodiment, the length of the axis 12 corresponds to the longitudinal extension of the patient support and positioning device 5, the start point 13 being oriented at the head end and the end point at the foot end 14 of the patient. It is of course possible that the movement of the acquisition arrangement also takes place the other way around and/or that the acquisition arrangement 2 moves along an axis 12 having a greater or smaller longitudinal extension. The movement of the acquisition arrangement 2 during an acquisition of a sequence of images can be controlled by the computing device 7 and be effected automatically.

What is to be understood as a spatial position of the acquisition arrangement 2 in the case of the X-ray device 1 shown in FIG. 1 is the position of a lengthening of a central ray 15 of the radiation field 11 to the axis 12. This position is indicated in FIG. 1 by the arrow 16. With the patient 6 positioned on the patient support and positioning device 5, the spatial position can in this case be assigned an anatomical position identified by the arrow 17. The anatomical position corresponds to the anatomical region of the patient 6 which can be scanned by the acquisition arrangement 2 in its current spatial position. In this case, analogously to the spatial position, the central ray 15 of the radiation field 11 generated by the X-ray tube assembly 3 is likewise made use of.

A method according to an embodiment of the invention for operating the X-ray device 1 provides that a sequence of images of the patient 6 is acquired while the acquisition arrangement 2 moves along the patient 6 in the scanning direction. During the acquisition of the individual images, the collimator aperture of the collimator 9 of the X-ray tube assembly 2 is adjusted as a function of position information describing a position of the acquisition arrangement 2, i.e. the individual images of the sequence of images are therefore acquired with different aperture angles 10, the size of the aperture angle 10 being dependent on the position information describing the position of the acquisition arrangement 2 in the scanning direction.

Figure 2:
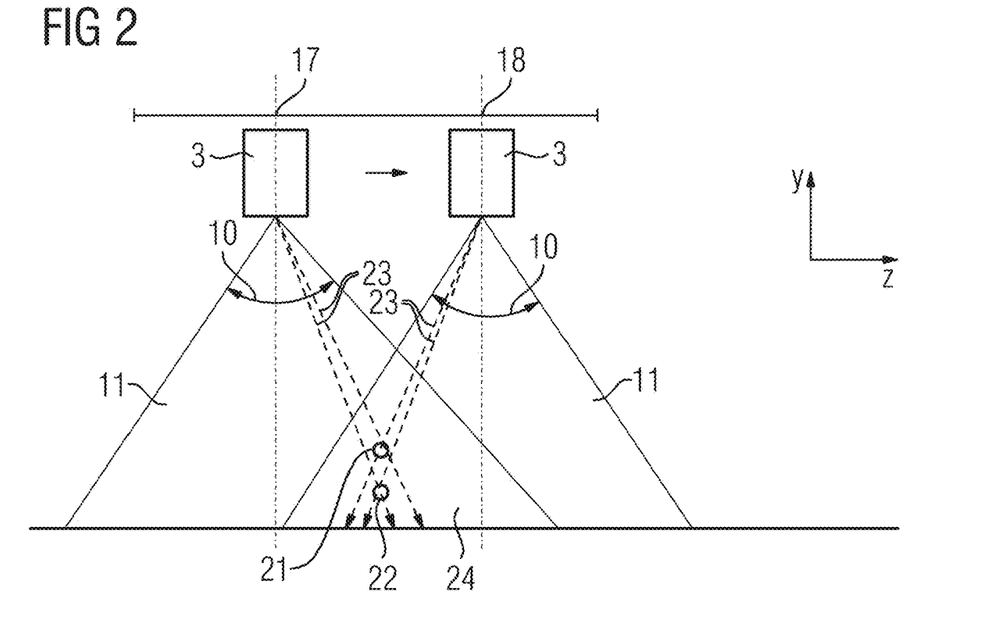
FIG. 2 shows a schematic representation of an image acquisition with large aperture angles.

The effect of the aperture angle 10 on an acquisition of images is explained below in connection with FIGS. 2 and 3. For clarity of illustration reasons, the X-ray tube assembly 3 is shown in each case in only two positions 17, 18, which are spaced apart in the scanning direction and are arrived at one after the other in time in the course of an acquisition of a sequence of images. In the situation shown in FIG. 2, the collimator is set in such a way that a comparatively wider aperture angle 10 of the radiation field 11 results. Because of the greater expansion of the radiation field 11 it is possible to study two anatomical structures 21, 22 arranged one above the other from different viewing directions, as is indicated by the dashed arrows 23. As a result of the images generated from clearly different viewing directions, it is possible to produce high-quality depth information in relation to the anatomical structures 21 and 22. For this purpose, the largest possible spatial overlap area 24 of the radiation field 11 from the positions 17 and 18 is desirable.

Figure 3:
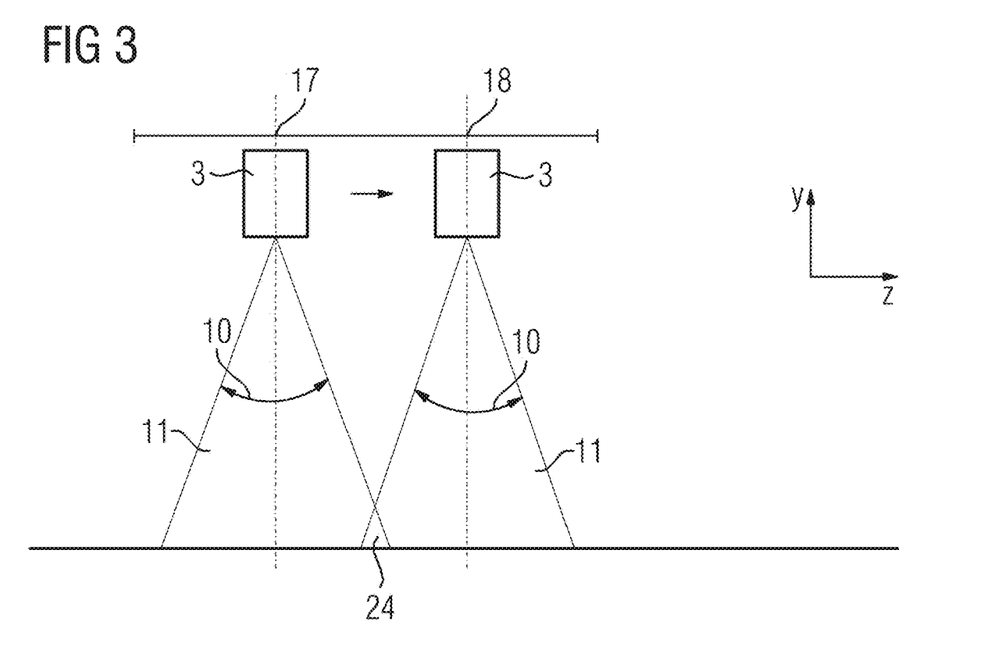
FIG. 3 shows a schematic representation of an image acquisition with a small aperture angle.

FIG. 3 shows an image acquisition in the positions 17, 18 using a smaller aperture angle 10 of the radiation field 11. Because of the smaller aperture angle 10, the spatial overlap area 24 is also reduced in size. Compared with the situation depicted in FIG. 2, the radiation exposure is reduced in the situation shown in FIG. 3 because only a smaller area is irradiated by the radiation field 11 for each image acquired in the positions 17 and 18.

Figure 4:
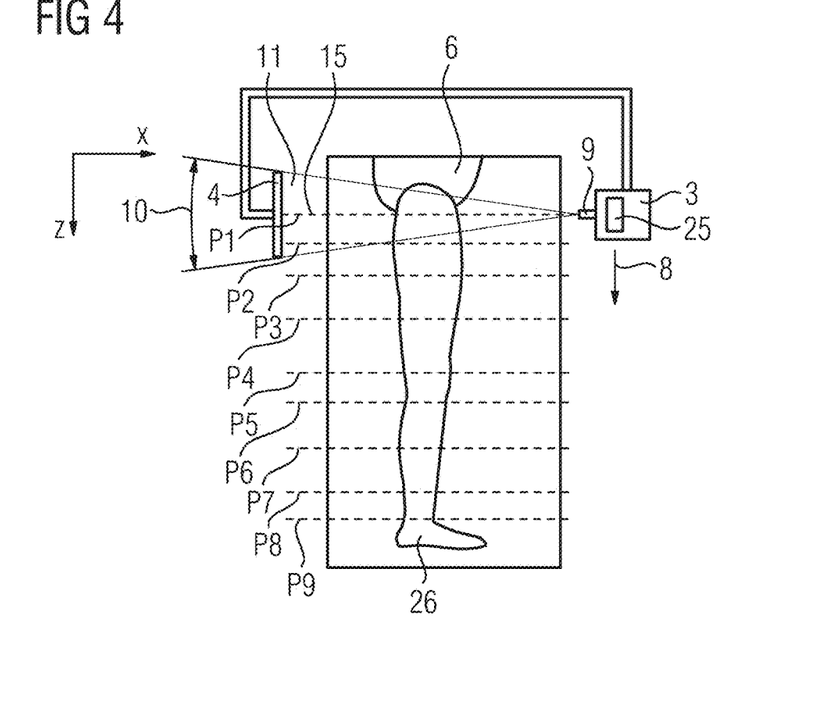
FIG. 4 shows a schematic representation of a step in a method according to an embodiment of the invention.

FIG. 4 illustrates a step in a method according to an embodiment of the invention. For the method according to an embodiment of the invention, it is provided that the aperture angle 10 of the collimator 9 of the X-ray tube assembly 3 is varied as a function of position information describing the position of the X-ray tube assembly 3 in the scanning direction. In this case the position information advantageously describes an anatomical position of the acquisition arrangement 2, i.e. the positioning of the acquisition arrangement 2 in relation to the patient 6.

An assignment of an anatomical position of the patient 6 to the spatial position of the acquisition arrangement 2 can be accomplished for example via a user input into the computing device 7 of the X-ray device 3. For example, the measurements of the patient 6 can be taken by an operator of the X-ray device 3 prior to the acquisition of the sequence of images in order to enable the anatomical position of the positioned patient to be assigned to the spatial positions of the acquisition arrangement 2.

It is also possible for a user of the X-ray device 1 to move the acquisition arrangement 2 manually and, when the spatial position coincides with an anatomical position, to store this assignment by way of a user input into the computing device 7 of the X-ray device 3. In addition or alternatively thereto, it is possible for the anatomical position of the acquisition arrangement 2 to be generated from image data acquired via an optical camera 25. In this case the optical camera 25 can be a part of the X-ray device 1 and be arranged either in a fixed location or as a component part of the acquisition arrangement 2, for example in spatial proximity to the X-ray tube assembly 3. For a current spatial position of the acquisition arrangement 2, the corresponding anatomical position of the patient 6 can be determined from the images generated by the optical camera 25, which is embodied for example as a 3D camera.

In addition or alternatively thereto, the anatomical position can also be determined from at least one already acquired image of the sequence of images. In the example embodiment described here, it is aimed to acquire a sequence of images showing a leg 26 of the patient 6. Here, starting at a hip of the patient and extending down to the foot, nine anatomical positions P1 to P9 are schematically indicated as dashed lines.

FIG. 4 shows the acquisition of an image in the hip region of the patient at position P1. Because of the spatially overlapping anatomical structures, such as the hip joint in the hip region of the patient 6, depth information is desired in this region. The image acquisition by the acquisition arrangement 2 is therefore carried out at the position P1 using a large aperture angle 10 of the radiation field 11, i.e. a large collimator aperture is set for the collimator 9 of the X-ray tube assembly 3.

Figure 5:
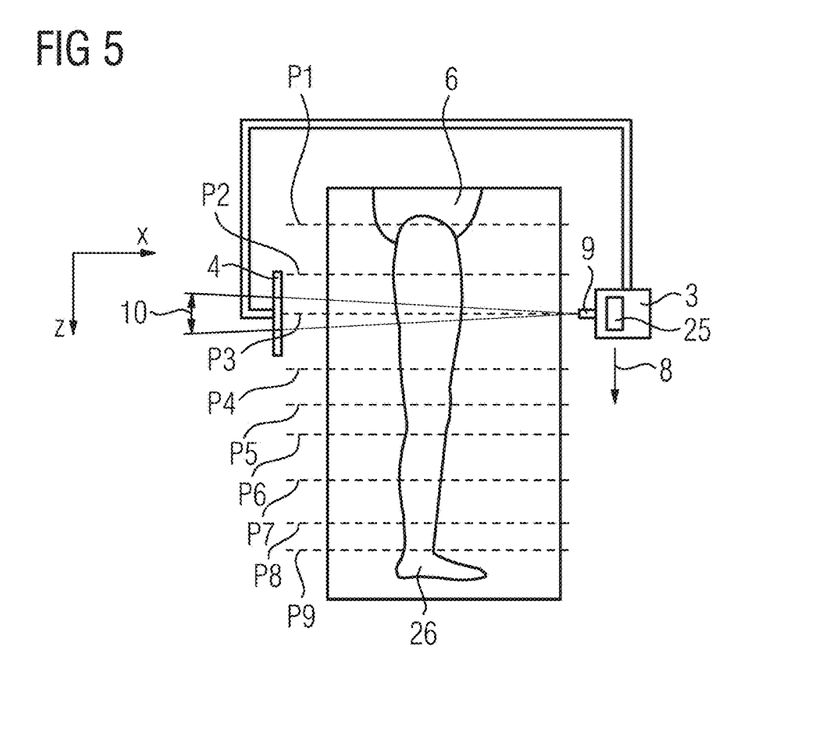
FIG. 5 shows a schematic representation of a further step in a method according to an embodiment of the invention.

FIG. 5 illustrates a further method step in the method according to an embodiment of the invention, in which an image is acquired in the middle of a thigh of the patient 6. Because there are no overlapping anatomical structures present when for example an image of a femoral shaft is acquired, no depth information is desired at the position P3 in this example, so the scan is performed with a reduced aperture angle 10 at this point in order to reduce the radiation exposure for the patient 6, i.e. the collimator 9 of the X-ray tube assembly 3 is therefore set to a small collimator aperture.

Different collimator apertures can therefore be used along the leg of the patient 6 for different positions P1 to P9. The collimator apertures to be used in each case or, as the case may be, the depth information to be generated in each case can be stored here in the computing device 7 of the X-ray device 1 as a function of the anatomical position. It is also possible for a corresponding assignment of collimator apertures to anatomical positions to be input into the computing device 7 by a user of the X-ray device 1 prior to the commencement of the image acquisition or for the same to be selected from a plurality of possible assignments.

Figure 6:
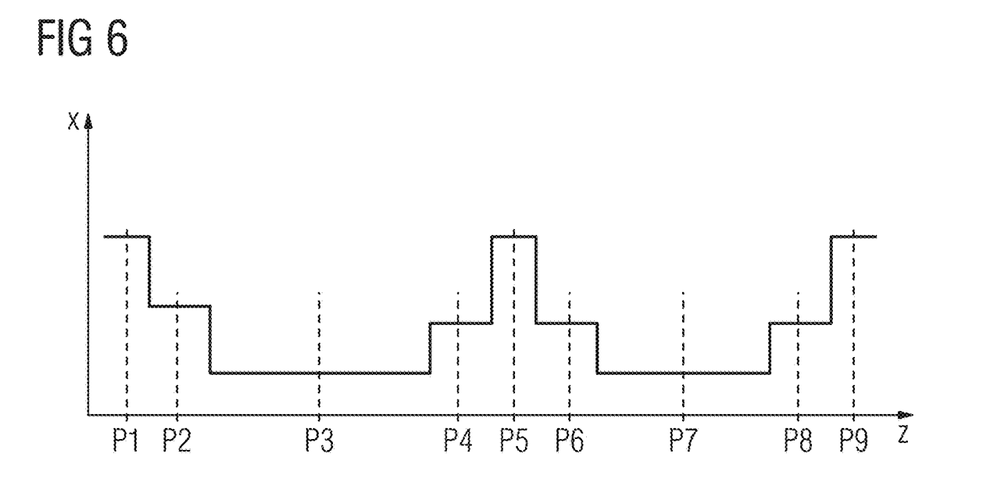
FIG. 6 shows a diagram representing the aperture angle of a collimator as a function of a scanning direction.

FIG. 6 shows a diagram which plots the collimator aperture, in this case designated by the letter a, in the scanning direction, in this case along the z-axis. In addition to a maximum collimator aperture in the positions P1, P5 and P9 as well as the minimum collimator aperture in the region of the positions P3 and P7, an intermediate value lying between the maximum collimator aperture and the minimum collimator aperture is set in this example at the positions P2, P4, P6 and P8.

Referring to the example shown in the preceding FIGS. 4 and 5, images are therefore acquired using a large collimator aperture in the hip region (P1), in the knee region (P5) and in the region of the ankle joint (P9) of the patient, and using a minimum collimator aperture in the region of the thigh (P3) and of the lower leg (P7). In the transitional regions between maximum and minimum collimator aperture (P2, P4, P6 and P8), a scan is performed using an intermediate value for the collimator aperture. The sequence of images acquired in the course of the method according to an embodiment of the invention can subsequently be processed and for example combined to construct a composite image.

It is of course possible for images to be acquired at a different number of positions and/or at positions different from those shown. It is also possible for no or more than one intermediate step of the collimator aperture to be chosen in order to obtain an aperture angle between maximum and minimum aperture angle 10.

Figure 7:
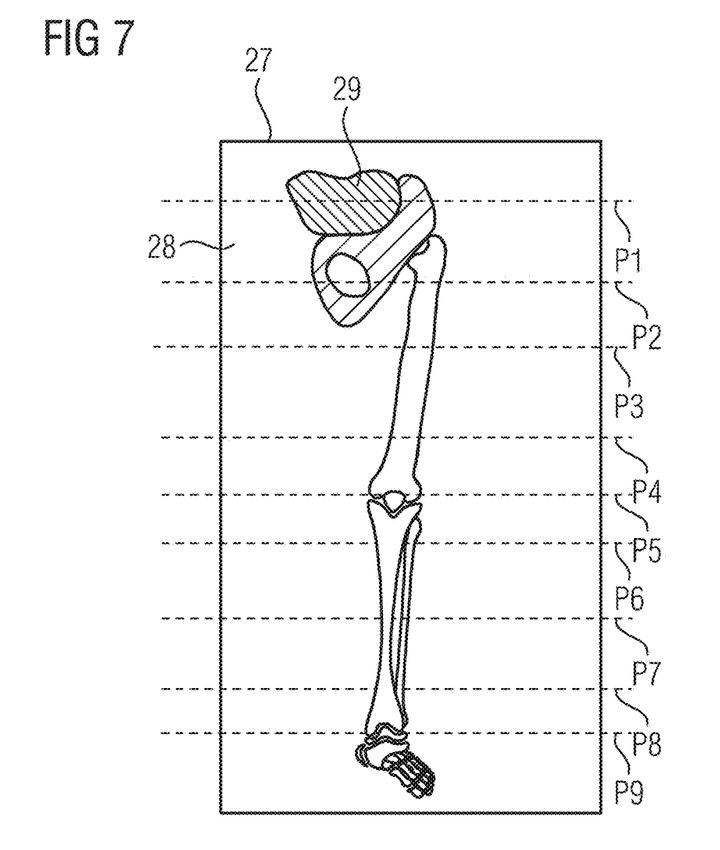
FIG. 7 shows a schematic representation of an overall image generated from a sequence of images acquired using the method according to an embodiment of the invention.

FIG. 7 shows an overall image 27 produced from the sequence of images acquired via the method according to an embodiment of the invention. The overall image 27 represents a 2D radiographic image supplemented by the depth information and is composed of a plurality of single images 28 from the sequence of acquired images. The depth information can be highlighted in color, for example, or, as in this case, by different hatchings 29. In this case the depth information can be indicated in particular in the regions that were previously acquired with a greater aperture angle 10, such as the region of the hip (P1), the knee (P5) and the ankle joint (P9). In addition or alternatively to the 2D radiographic image, a 3D tomosynthesis dataset can be generated which contains a 3D model at least for some of the anatomical structures represented on the images.

It is possible to produce both a 2D radiographic image and a 3D tomosynthesis dataset. In this case the 2D radiographic image, for example, can be displayed to a user of the X-ray device, the user being able to select by way of a user input a region or an anatomical structure represented in the 2D image, a 3D representation of the selected region or of the anatomical feature generated from the 3D tomosynthesis dataset subsequently being able to be displayed to the user. Anatomical landmarks can also be determined in the representation generated from the sequence of images. Thus, for example, during the scan of a patient's leg, a plurality of landmarks can be used in order to check for the presence of genu valgum (knock-knees) and genu varum (bowlegs) via a measurement, such as a deviation of the Mikulicz line.

It is of course also possible to establish a different assignment of collimator apertures to anatomical structures from that described in the preceding example. For example, it may also be desired to generate depth information in the thigh region, for example in the event of a femoral fracture being present in this region, and in the surrounding regions, such as in the knee and the hip, for example, no depth information is necessary for the medical issue in question.

Although the invention has been illustrated and described in more detail on the basis of the preferred example embodiment, the invention is not limited by the disclosed examples and other variations may be derived herefrom by the person skilled in the art without leaving the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 X-ray device
2 Acquisition arrangement
3 X-ray tube assembly
4 X-ray detector
5 Patient support and positioning device
6 Patient
7 Computing device
8 Arrow
9 Collimator
10 Aperture angle
11 X-ray field
12 Axis
13 Start point
14 End point
15 Central ray
16 Arrow
17 Position
18 Position
21 Structure
22 Structure
23 Arrow
24 Overlap area
25 Camera
26 Leg
27 Overall image
28 Image
29 Hatching
P1-P9 Position

What is claimed is:

1. A method for operating an X-ray device, the method comprising:
    acquiring a sequence of images of a patient;
    moving an acquisition arrangement including at least one X-ray tube assembly, during the acquiring of the sequence of images, along the patient in a scanning direction;
    wherein individual images of the sequence of images are acquired at different positions in the acquisition arrangement and each represent a different segment of the patient;
    evaluating at least two different images, showing at least one common feature of the patient, to determine depth information for the at least one common feature; and
    actuating a collimator aperture of a collimator of the X-ray tube assembly, as a function of position information describing a position of the acquisition arrangement in the scanning direction, to change an aperture angle of a radiation field generated by the X-ray tube assembly in the scanning direction.

2. The method of claim 1, wherein the position information describes an anatomical position describing a current positioning of the acquisition arrangement in relation to the patient.

3. The method of claim 2, wherein the anatomical position is determined from at least one of
    image data acquired via an optical camera of the X-ray device, and
    at least one already acquired image of the sequence of images.

4. The method of claim 2, wherein the anatomical position is determined from a spatial position describing a current distance of the acquisition arrangement from a start point or an end point of the moving of the acquisition arrangement.

5. The method of claim 4, wherein different anatomical positions are assigned to different spatial positions via at least one of
    a received user input into a computing device of the X-ray device; and
    a manual moving of the acquisition arrangement into a spatial position corresponding to an anatomical position.

6. The method of claim 1, wherein an anatomical landmark is determined from at least one image of the sequence of images, and wherein at least one item of depth information is determined for the anatomical landmark.

7. The method of claim 1, wherein the collimator aperture is assigned to an anatomical position as a function of assignment information stored in a computing device of the X-ray device.

8. The method of claim 1, wherein the collimator aperture of the collimator of the X-ray tube assembly is actuated orthogonally to the scanning direction as a function of the position information to change an aperture angle of the radiation field generated by the X-ray tube assembly.

9. The method of claim 1, wherein at least one further acquisition parameter of the X-ray device is varied in addition to the collimator aperture of the collimator of the X-ray tube assembly.

10. The method of claim 1, wherein an acquisition arrangement is used including at least one X-ray detector disposed opposite the at least one X-ray tube assembly, and wherein at least one further acquisition parameter of the at least one X-ray detector is set as a function of the position information.

11. The method of claim 10, wherein at least one of a collimator aperture of a collimator of the X-ray detector, a detector entrance dose, an X-ray focus-detector distance, and an angle formed by a central ray of the radiation field and a detector normal of the X-ray detector is varied as the at least one further acquisition parameter of the X-ray detector.

12. The method of claim 1, wherein a synthetic radiographic image, supplemented by at least one item of depth information of a relevant anatomical region as supplementary information, is generated from the sequence of images.

13. An X-ray device, comprising:
an acquisition arrangement, including at least one X-ray tube assembly including a collimator; and
a computing device, configured to
acquire a sequence of images of a patient;
move an acquisition arrangement including at least one X-ray tube assembly, during acquisition of the sequence of images, along the patient in a scanning direction;
wherein individual images of the sequence of images are acquired at different positions in the acquisition arrangement and each represent a different segment of the patient;
evaluate at least two different images, showing at least one common feature of the patient, to determine depth information for the at least one common feature; and
actuate a collimator aperture of a collimator of the X-ray tube assembly, as a function of position information describing a position of the acquisition arrangement in the scanning direction, to change an aperture angle of a radiation field generated by the X-ray tube assembly in the scanning direction.

14. A non-transitory electronically readable storage medium comprising instructions which, when executed by a computing device of an X-ray device, cause the computing device to carry out the method of claim 1.

15. The method of claim 3, wherein the anatomical position is determined from a spatial position describing a current distance of the acquisition arrangement from a start point or an end point of the moving of the acquisition arrangement.

16. The method of claim 15, wherein different anatomical positions are assigned to different spatial positions via at least one of
a received user input into a computing device of the X-ray device; and
a manual moving of the acquisition arrangement into a spatial position corresponding to an anatomical position.

17. The method of claim 2, wherein the collimator aperture of the collimator of the X-ray tube assembly is actuated orthogonally to the scanning direction as a function of the position information to change an aperture angle of the radiation field generated by the X-ray tube assembly.

18. The method of claim 9, wherein at least one of a scanning speed of the acquisition arrangement, a tube current-time product of the X-ray tube assembly, an electrical voltage of the X-ray tube assembly and an X-ray focus-patient distance of the X-ray tube assembly is used the at least one further acquisition parameter.

19. The method of claim 12, a 3D tomosynthesis dataset is generated from the sequence of images.

20. The X-ray device of claim 13, wherein an acquisition arrangement is used including at least one X-ray detector disposed opposite the at least one X-ray tube assembly, and wherein at least one further acquisition parameter of the at least one X-ray detector is set as a function of the position information.

21. The X-ray device of claim 20, wherein at least one of a collimator aperture of a collimator of the X-ray detector, a detector entrance dose, an X-ray focus-detector distance, and an angle formed by a central ray of the radiation field and a detector normal of the X-ray detector is varied as the at least one further acquisition parameter of the X-ray detector.

* * * * *

UNITED STATES PATENT AND TRADEMARK OFFICE
CERTIFICATE OF CORRECTION

| | |
|---|---|
| PATENT NO. | : 10,660,581 B2 |
| APPLICATION NO. | : 16/519129 |
| DATED | : May 26, 2020 |
| INVENTOR(S) | : Andreas Fieselmann et al. |

It is certified that error appears in the above-identified patent and that said Letters Patent is hereby corrected as shown below:

On the Title Page

Item (30), Column 1, should read:
Foreign Application Priority Data
(30) Jul. 25, 2018 (DE)...................... 10 2018 212 389.6

Signed and Sealed this
Seventh Day of July, 2020

Andrei Iancu
*Director of the United States Patent and Trademark Office*